United States Patent
Miklavcic et al.

(10) Patent No.: US 7,625,729 B2
(45) Date of Patent: Dec. 1, 2009

(54) ELECTROPORATION DEVICE

(75) Inventors: Damijan Miklavcic, Ljubljana (SI); Lluis Mir, Villejuif (FR)

(73) Assignee: IGEA S.r.l. (IT)

( * ) Notice: Subject to any disclaimer, the term of this patent is extended or adjusted under 35 U.S.C. 154(b) by 523 days.

(21) Appl. No.: 10/517,038

(22) PCT Filed: Jun. 10, 2003

(86) PCT No.: PCT/EP03/05993

§ 371 (c)(1),
(2), (4) Date: Aug. 25, 2005

(87) PCT Pub. No.: WO03/104448

PCT Pub. Date: Dec. 18, 2003

(65) Prior Publication Data

US 2006/0057706 A1    Mar. 16, 2006

(30) Foreign Application Priority Data

Jun. 7, 2002    (IT)    ............................ TO2002A0477

(51) Int. Cl.
    *C12N 13/00*    (2006.01)
(52) U.S. Cl. .............. 435/173.6; 435/173.4; 435/173.5; 435/285.2; 435/461; 204/403.01; 205/777.5
(58) Field of Classification Search .............. 435/285.2, 435/460, 173.6, 461, 470; 800/292
See application file for complete search history.

(56) References Cited

U.S. PATENT DOCUMENTS 6,653,091 B1 *  11/2003  Dunn et al. .................. 435/14

FOREIGN PATENT DOCUMENTS

| WO | 01 07583 A | 2/2001 |
|----|------------|--------|
| WO | 01 07584 A | 2/2001 |
| WO | 01 07585 A | 2/2001 |
| WO | 01 81533 A | 11/2001 |

OTHER PUBLICATIONS

International Search Report for International Application No. PCT/EP03/05993 dated Oct. 30, 2003.

* cited by examiner

*Primary Examiner*—William H Beisner
*Assistant Examiner*—Michael Hobbs
(74) *Attorney, Agent, or Firm*—Ostrolenk Faber LLP

(57) ABSTRACT

Electro-poration device for the permeabilization of cells contained in a substrate comprising a signal generator for generating a stimulating signal applied by means of electrodes to the substrate wherein an electric field permeabilizing the cells membranes is induced. The device calculates and monitors the instantaneous value or the ratio GT between the current flowing through the substrate and the voltage of the stimulating signal applied to the substrate; in particular, the stimulating signal is applied in a modified manner according to the shape of an initial portion of the waveform of a curve CGT representing the value of ratio GT in successive instants after the application of the stimulating signal. The system will achieve permeabilization of cells in substrate with no or minimum damage, allowing to introduce or to extract molecules in or from the electropermeabilized living cells.

14 Claims, 4 Drawing Sheets

ELECTROPORATION DEVICE

TECHNICAL FIELD

The above invention relates to an electro-poration device.

BACKGROUND ART

As it is known, recent biological, microbiological and pharmacological applications involve introducing molecules into cells, which is done by introducing the molecules through the cell membranes.

The molecules may be inorganic substances (e.g. drugs) or organic molecules (DNA molecules for example are known to be introduced in cells).

In order to introduce the molecules, the so-called electroporation methods have recently been devised, which are based on the application of electric pulses to the cells in order to produce an electric field that permeabilizes the cell structure enabling the substances to penetrate the cell membrane.

For instance PCT patent application WO01/07583 describes an Electro-poration device wherein an electrical voltage is applied to a substrate comprising cells and a current is flowing through the substrate. The above patent application also proposes to continuously detect the ratio of the current through the substrate to the voltage across the substrate as an indication of the obtained degree of electroporation of the substrate.

Finally, application WO01/07583 proposes to adjust the magnitude of the applied voltage in accordance with changes in the above ratio to achieve a controlled degree of electroporation in the substrate.

However, patent application WO01/07583 does not teach how to use the information related to the above ratio in order to have useful information for controlling the voltage; in other words, WO01/07583 merely discloses the possibility of controlling the voltage based on the detection of the above ratio but does not provide any real indication for creating a working system wherein the control of the voltage is successfully performed.

DISCLOSURE OF INVENTION

Scope of the present invention is to provide a working electroporation device wherein the control of the voltage applied to the substrate is obtained by means of the continues monitoring of the ratio of the current flowing through the substrate and the voltage applied to the substrate.

According to another embodiment of the present invention, the control of the voltage is obtained by simply monitoring the current.

The above scope is obtained by the present invention as it relates to an electro poration device as described in claim 1 or 13.

BRIEF DESCRIPTION OF THE DRAWINGS

The invention shall be described in accordance with the attached drawings which show a non-limiting embodiment of the invention wherein.

BEST MODE FOR CARRYING OUT THE INVENTION

Figure 1:
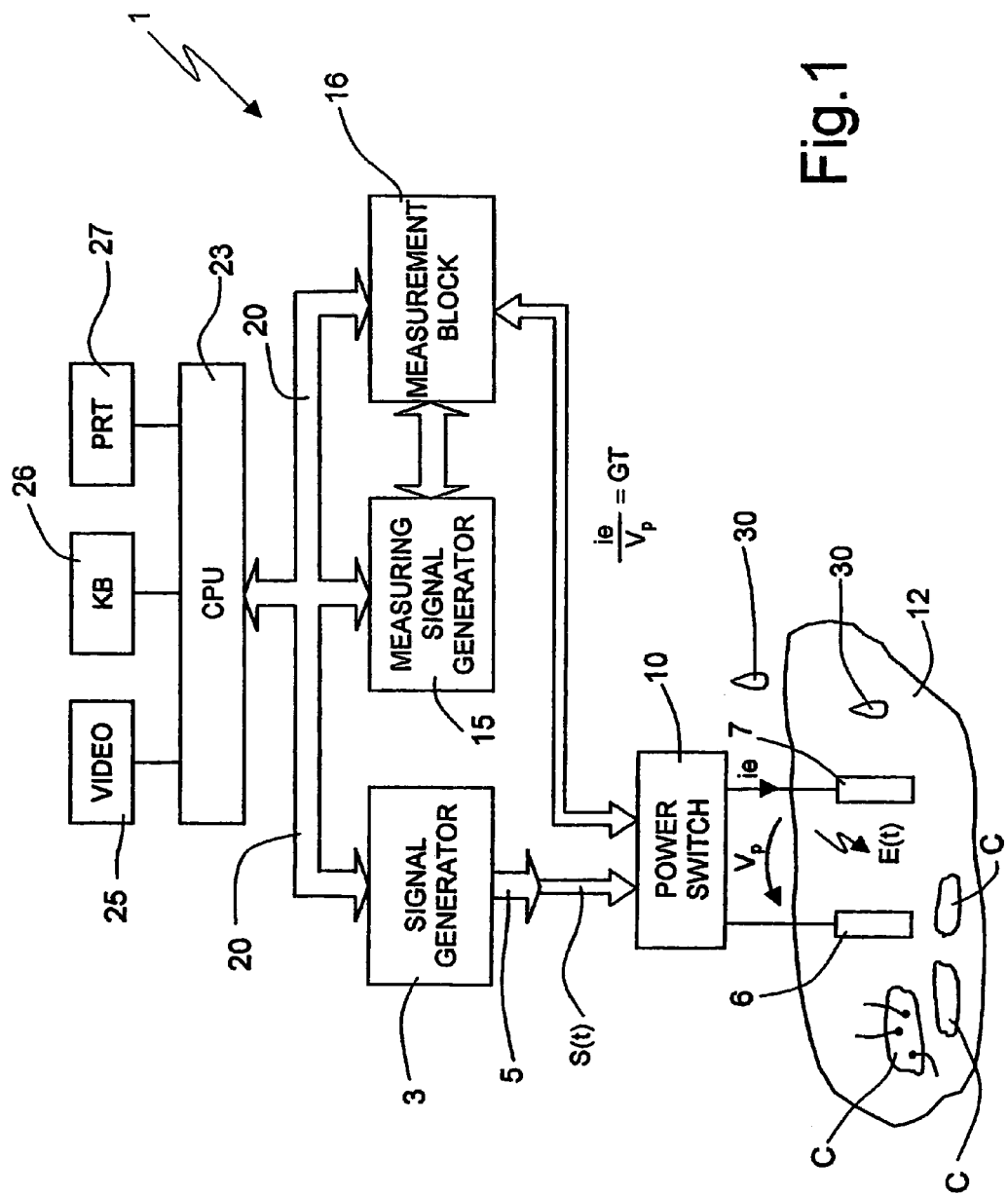
FIG. 1 shows, in a simplified manner, an electroporation device according to the present invention.

In FIG. 1, number 1 indicates an electro-poration device realised according to the present invention.

In particular, device 1 comprises of a signal generator 3 for producing a stimulating signal S(t) that is amplified by a power amplifier 5 and applied to electrodes 6, 7 through a power switch 10. The electrodes 6, 7 are coupled with a substrate 12 containing living cells C; in particular, the substrate 12 may comprise a portion (for instance a tissue) of a living body (plant, animal or man) or may comprise a substrate separate from the living body and contained in a recipient (for instance a culture of animal, plant, bacterial or fungal cells in vitro).

The application of the electroporating signal S(t) to the electrodes 6, 7 causes the creation of an electric field E(t) in the substrate 12; such a field E(t) promotes, realises or enhances the permeabilization of the membranes of the cells C rendering possible the introduction of molecules (organic/inorganic) through the membranes of the cells C.

Device 1 also comprises a measuring signal generator 15 coupled with a measurement block 16 co-operating with electrodes 6, 7 for the determination of the instantaneous values of the current through the substrate 12, the voltage actually applied to the substrate 12, and the ratio GT of the current through to voltage applied to the substrate 12 (i.e. $GT=i_e/v_p$).

Signal generator 3, measuring signal generator 15 and measurement block 16 are connected, through a common BUS 20, with a central processing unit 23 coupled with interface circuits (not shown), for the communication with peripheral devices, such as a video display 25, keyboard 26 and printer 27.

Under the control of the central processing unit 23 the signal generator 3 generates a signal S(t) comprising one or a series of pulses which amplitude may be regulated as described in the following. Moreover, the central processing unit 23 receives the information related to the Voltage $V_p$ of the stimulating signal S(t) applied to the electrodes 6, 7 and the current $i_e$ that flows between the electrodes 6, 7 through the substrate 12. More particularly, central processing unit 23 detects the instantaneous value of the ratio GT of the current $i_e$ flowing through the substrate 12 and the voltage $V_p$ applied to the substrate 12, i.e.: $GT=i_e/v_p$. and determines the instantaneous value of the signal S(t).

Figure 2:
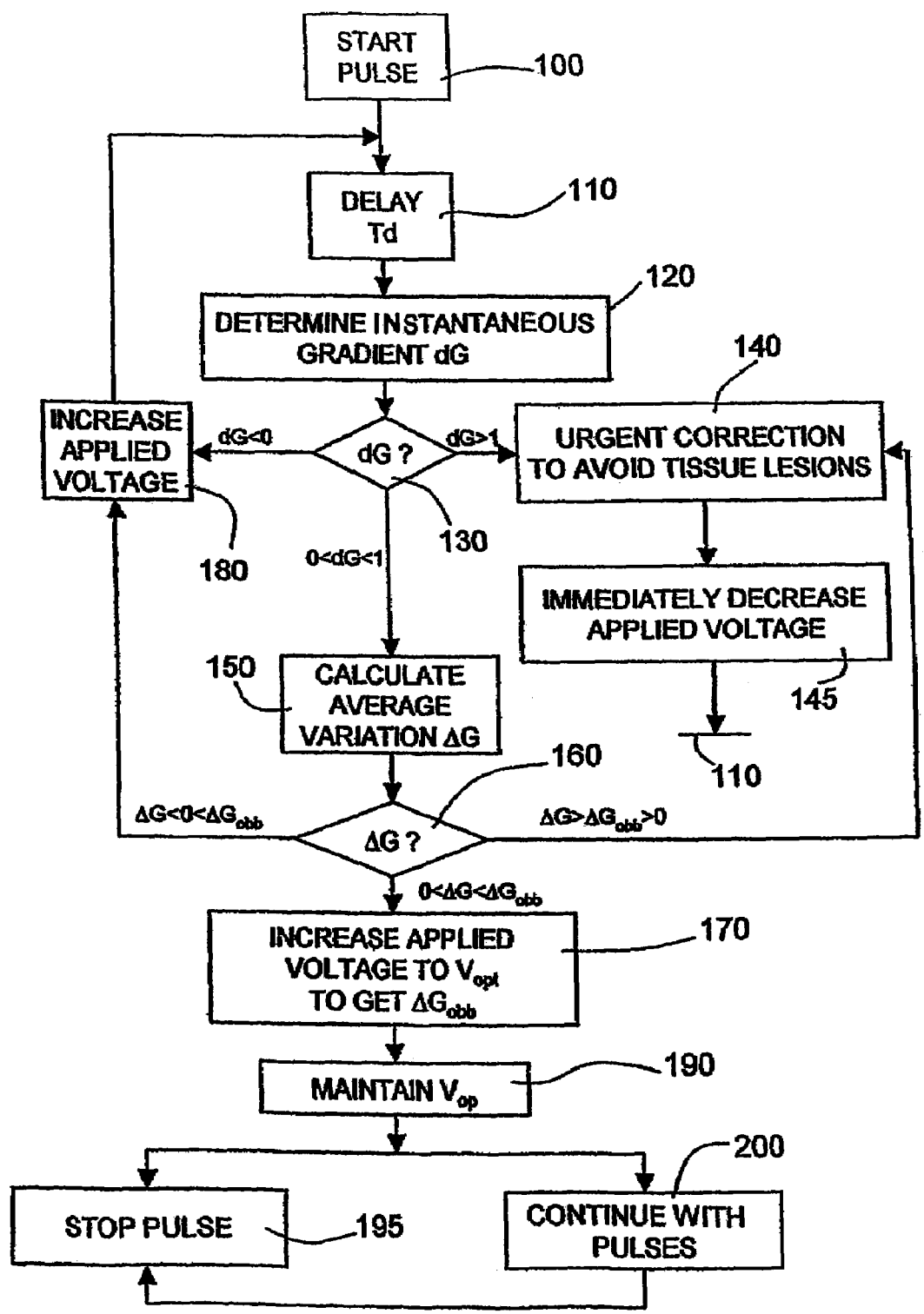
FIG. 2 is a flow chart of the operations performed by the electro poration device according to a first embodiment of the invention.

The knowledge of the above ratio GT is used for controlling stimulating signal S(t) as described in the flow chart of FIG. 2.

Figure 3:
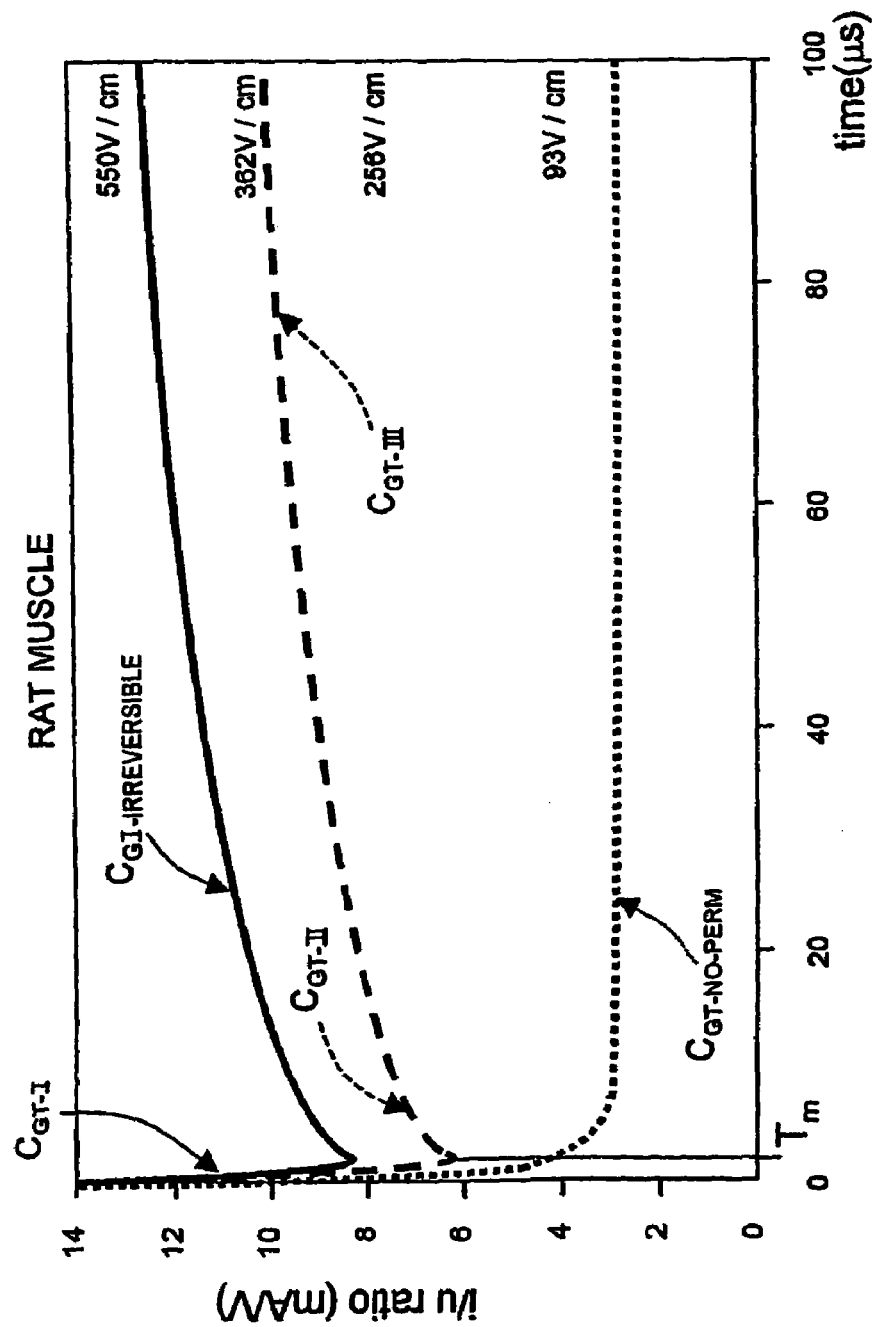
FIG. 3 illustrates a signal ratio of current to voltage based on which the control of the electroporating pulse S(t) is performed.

Studies and experiments of the applicant have revealed that the curve $C_{GT}$ representing the value of ratio GT in successive instants after the application of the stimulating signal S(t) has a particular waveform that is shown, as non limiting example, in FIG. 3.

In the Cartesian presentation of FIG. 3, Y-axis represents increasing values or ratio GT and X-axis represents successive instants after the start of the application of the stimulating signal S(t); the stimulating signal S(t) being applied from time t=0 on.

Curve $C_{GT}$ (if permeabilization process is in progress) comprises a first portion $C_{GT}$-I decreasing from time t=0 to a time t=Tm wherein an initial minimum is reached, a second portion $C_{GT}$-II increasing from the time Tm wherein the minimum is reached, and a third portion $C_{GT}$-III increasing with a very low rate or being substantially flat.

Curve $C_{GT}$ (if permeabilization is not achieved and permeabilization process in not in progress) comprises a first portion $C_{GT}$-I decreasing from time t=0 (the second portion $C_{GT}$-II increasing from the time Tm is absent) and a third portion $C_{GT}$-III decreasing with a very low rate or being substantially flat.

In particular, block 100 of FIG. 2 commands the generation of the stimulating signal S(t) and the application of such a signal S(t) to the substrate 12 through electrodes 6 and 7.

Block 100 is followed by a block 110, which functions as a timing element such that it introduces a delay Td so that the stimulating signal S(t) is applied for at least a predetermined period of time Td; such a period of time Td having a value so that ratio GT has time to reach and overcome its initial minimum value Tm, in particular ratio GT at the end of delay Td is placed on the second portion $C_{GT\text{-}II}$ of curve $C_{GT}$.

Block 110 is followed by block 120 that determines the instantaneous gradient dG (i.e. instantaneous slope) of the ratio GT after the minimum has been reached, i.e. calculates the derivative of ratio GT, dG=d(GT)/d(t), at the beginning of the second portion $C_{GT}$-II, or more practically the difference deltaG=deltaGT/deltaT at Tm.

Block 120 is followed by block 130 that compares the calculated instantaneous variation dG of the ratio GT with a reference value $dG_{ref1}$, for instance $dG_{ref1}=1$.

In particular, if the calculated instantaneous variation dG of the ratio GT is greater than the reference value $dG_{ref1}$ (for instance dG>1) block 130 is followed by block 140. If the applied signal S(t) is of too small amplitude to initiate the process of permeabilization the first minimum is not reached within the predetermined time Tm and the gradient at Td is lower than a predetermined $dG_{ref2}$, for instance $dG_{ref2}=0$, the dG at Td is negative (dG<0) and block 130 is followed by block 180, whilst if the calculated instantaneous variation dG of the ratio GT is smaller than the reference value $dG_{ref1}$ and at the same time larger than $dG_{ref2}$ (for instance 0<dG<1) block 130 is followed by block 150.

Block 140 performs an urgent correction to the stimulating signal S(t) in order to avoid lesions, damages or irreversible alterations in substrate 12; to that regard block 140 is followed by a block 145 that decreases the amplitude (i.e. the voltage) of the stimulating signal S(t) in order to prevent deterioration in the cells C. Block 145 is then followed by block 110.

Block 150 calculates the average variation ΔG of ratio GT (i.e. the slope calculated over a period of time) in a time interval that is successive to the instant Tm wherein the minimum has been reached and that has a pre-determined time width, for instance ΔG=ΔGT/(T1−Tm) wherein T1>Tm.

Block 150 is followed by a block 160 that compares the calculated average variation ΔG of ratio GT with a reference interval of ΔG values, for instance a reference interval having limits 0 and $\Delta G_{obb}$, wherein $\Delta G_{obb}$ is an expected value of the average variation ΔG above which the corresponding pulses will lead to a too intense permeabilization of the cells and to subsequent damages to the cells.

In particular block 160 performs the following functions:
if the calculated average variation ΔG of ratio GT falls within the reference interval (for instance $0<\Delta G<\Delta G_{obb}$) then block 160 is followed by a block 170;
if the calculated average variation ΔG of ratio GT falls outside the reference interval and it is smaller than both the limits delimiting the interval (for instance $\Delta G<0<\Delta G_{obb}$) then block 160 is followed by a block 180; and
if the calculated average variation ΔG of ratio GT falls outside the reference interval and it is greater than both the limits delimiting the interval (for instance $\Delta G>\Delta G_{obb}>0$) then block 160 is followed by block 140.

Block 180 increases the voltage of the stimulating signal in order to increase the value of the electric field E(t) applied to the substrate 12; block 180 is then followed by block 110.

Block 170 increases the voltage of the stimulating signal to an objective voltage $V_{opt}$ in order to increase the value of the electric field E(t) applied to the substrate 12 so that the value of ΔG tends to the expected value $\Delta G_{obb}$.

The operational process of blocks 100-180 and associated device elements comprise controlling elements for applying the stimulating signal in a controlled manner.

When the objective voltage $V_{opt}$ has been reached block 170 is followed by a block 190 that maintains the stimulating signal at the objective voltage $V_{opt}$ for a predetermined time that is sufficient for achieving a complete electroporation of cells C.

Finally, block 190 may be followed by a block 195 that stops the application of pulses of the stimulating signal S(t) or by a block 200 that, if needed, continues for an extra period of time the application of the stimulating signal of the same or of another value (for example, lower), depending on the molecule to be introduced.

Figure 4:
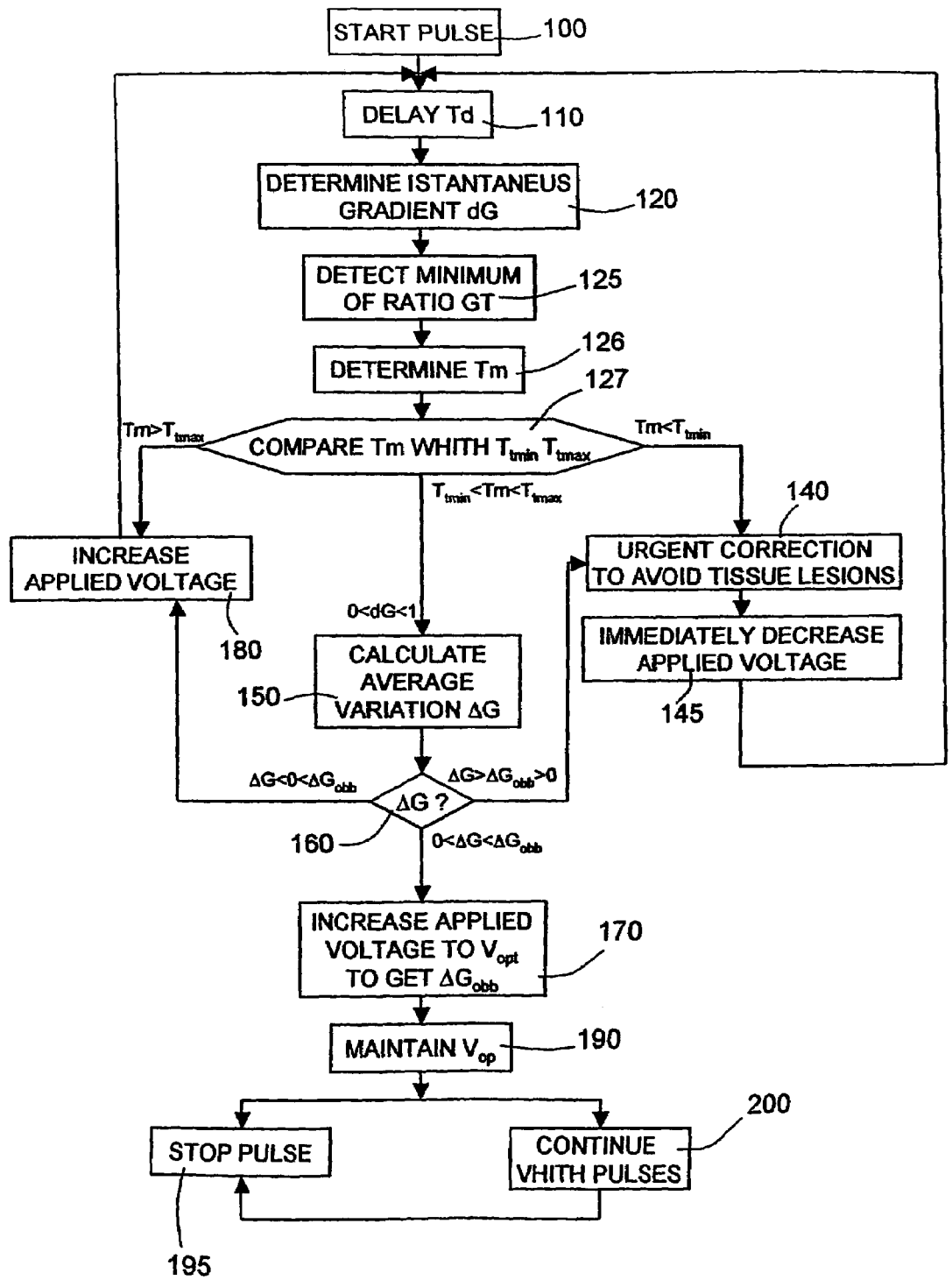
FIG. 4 is a flow chart of the operations performed by the electro poration device according to a second embodiment of the invention.

FIG. 4 shows another preferred embodiment of the present invention. The operations that have not been modified have been indicated by blocks having the same reference numbers, and different operations are indicated with new block and numbers.

More particularly, block 120 is followed by block 125 that detects the minimum of the ratio GT. This operation may be realized according know techniques for instance by comparing the instantaneous gradient dG calculated with previously recorded gradients.

Block 125 is followed by block 126 that determines the time Tm at which the minimum detected by block 125 occurs.

Block 126 is followed by block 127 that compares the detected time Tm with threshold values Ttmin and Ttmax.

More particularly, if the detected Tm occurs before Ttmin (Tm<Ttmin) then block 126 is followed by block 140.

If the detected Tm occurs after Ttmax (Tm>Ttmax), then block 126 is followed by block 180.

If Tm occurs between Ttmin and Ttmax, then block 126 is followed by block 150. Accordingly block 130 is eliminated.

In actual use, electrodes 6, 7 are applied to the substrate 12 (shown schematically in FIG. 1) containing live cells C. As above outlined, the substrate 12 may comprise a tissue portion forming part of a live being (human, animal or plant) or may comprise a tissue or a culture of cells (animal or plant) separated from a live being or a culture of micro-organisms (bacteria or fungi, e.g. yeast).

Substrate 12 is also applied with a substance (organic or inorganic or biopolymeric) 30 to be introduced into the cells C. The substance 30 may be applied in a number of different ways, some of which are listed below by way of non-limiting examples:
direct application of the substance to the substrate 12, e.g. by applying to the substrate a fluid containing the substance;
indirect application of the substance, e.g. by introducing the substance into the circulatory system of the tissue portion forming the substrate; and injecting the substance, e.g. using needlelike electrodes 6, 7 (not shown), each having an inner conduit containing the substance to be injected into the tissue portion forming the substrate. The substance may also be injected using needles separate from the electrodes.

The substance 30 introduced may be inorganic or organic or biopolymeric, e.g a nucleic acid; a DNA molecule containing regulatory sequences and sequence coding for therapeutic genes or genes of interest for biomedical or biotechnological purposes; an oligonucleotide, whether natural (phosphodiesters) or modified (inside the backbone of the oligonucleotide, such as phosphosulfates, or at the extremities, by addition of groups to protect the oligonucleotides from digestion of nucleases; the description of oligonucleotide modifications being non-limiting); a protein or peptide, whether natural or genetically or chemically modified, extracted from natural sources or obtained by synthesis, or a molecule simulating the structure of a protein or peptide, whatever its structure; a cytotoxic agent, in particular, the antibiotic bleomycin or the cisplatinum; a penicillin; and other pharmacological agents. The substrate 12 can also be treated without the application of a substance when the purpose is to extract from the cells C a molecule (organic or inorganic or biopolymeric) contained in or produced by the living cells C. In particular, the production of proteins or small organic molecules produced by genetically modified cells or genetically selected cells could be collected from the producing cells by the controlled procedure achieved by the device here described. Extraction of substances such as the molecules from cells C can be achieved by extraction means such as diffusion through the permeabilized membranes, by reverse iontophoresis or by any other active, passive or combined mechanism Electroporation device 1 is activated to generate one pulse or a train of pulses (block 100) that are spaced one with respect the other. Electroporation of the cells is therefore started and the ratio GT begins to fall following the first portion of curve $C_{GT}$ (i.e. $C_{GT}$-I).

Pulses are applied for a period of time (block 110) so that ratio GT reaches its minimum at the time Tm; for instance period Td may be 15 µs.

Then to avoid damages in the cells an immediate check is performed (by hazard detecting elements of blocks 120 and 130) to see if, after the minimum has been reached, curve $C_{GT}$ has a too rapid increase (dG>1); in fact, a too rapid increase after the minimum is a clear indication of irreversible damages to the cells (to that regard see curve $C_{GT\text{-}IRREVERSIBLE}$ shown in FIG. 3). In case of a detected indication of irreversible damages a corrective action is performed (blocks 140 and 145) by immediately decreasing the voltage applied thus preventing final damage to the cells. The check of hazard detecting elements of blocks 120, 130 may be substituted (or integrated) by the check of blocks 126 and 127.

In case that no indication of damage is detected then the average slope of curve $C_{GT}$ is scrutinised (block 150) to see if and how the cells are being permealized. In particular:

if the calculated average variation $\Delta G$ of ratio GT falls within the reference interval ($0<\Delta G<\Delta G_{obb}$) a situation of normal beginning of the process of permeabilization of the cells is detected and the process of permeabilization is normally continued by increasing the voltage (block 170) so that the value of $\Delta G$ tends to the expected value $\Delta G_{obb}$;

if the calculated average variation $\Delta G$ of ratio GT falls outside the reference interval and it is smaller than both limits delimiting the interval ($\Delta G<0<\Delta G_{obb}$) no beginning of permeabilization is detected (with this regard see curve $C_{GT\text{-}NO\text{-}PERM}$) and the voltage is increased (block 180) to start the process of permeabilization; and if the calculated average variation $\Delta G$ of ratio GT falls outside the reference interval and it is greater than both limits delimiting the interval ($\Delta G>\Delta G_{obb}>0$) a potentially dangerous situation is detected and a corrective action is consequently performed (blocks 140 and 145).

The above operation may also be performed by using, instead of the ratio $GT=i_e/v_p$, any mathematical combination of current $i_e$ and voltage $v_p$.

Moreover, the above operations may also be performed by using, instead of any mathematical combination of current $i_e$ and voltage $v_p$, the value of the current $i_e$. In fact, current $i_e$ has a shape that is very similar to the shape of ratio GT presented in FIG. 3 if Vp rise times is very fast and if Vp is then constant or almost constant.

In the above case all the operations disclosed with respect to blocks 100-200 directly performed on the current ie. For instance block 120 determines the instantaneous variation die of current ie, block 130 compares the instantaneous variation die with reference values, block 150 calculates an average variation Δie of current ie and block 160 compares the calculated average variation Δie with reference values.

According to the above embodiment, it is necessary a more simple equipment for measure and calculation and the electroporation device provide a stimulating signal extremely "square".

It is therefore clear that, according to the present invention, the curve $C_{GT}$ is constantly monitored and the stimulating signal is applied in a modified manner according to the detected waveform of an initial portion of curve $C_{GT}$.

In particular, the application of the stimulating signal is dependent on the shape of the curve $C_{GT}$, in particular the slope at particular time points.

Studies and experiments performed by the applicant have revealed that controlling the process of permeabilization as above outlined, i.e. focusing the analysis in the initial part of the waveform that corresponds to the initial instants wherein the process has been started but the real permeabilization has not still occurred, permits from one side to avoid damages to the cells and from the other side to obtain a good permeabilization of the cells.

The invention claimed is:

1. Electroporation device for the permeabilization of cells (C) contained in a substrate comprising a signal generator configured for generating a stimulating signal (S(t)) applied by means of electrodes to the substrate wherein an electric field (E(t)) permeabilizing the cells membranes is induced; the device comprising:
   an element configured for measuring, calculating and monitoring the instantaneous value of the ratio (GT) of current (ie) flowing between said electrodes and through the substrate and the voltage (Vp) of the stimulating signal (S(t)) applied to the substrate by means of said electrodes;
   said device further comprising a controlling element configured for applying the stimulating signal in a controlled manner according to the waveform of only an initial portion of the curve $C_{GT}$ representing the ratio (GT) in successive instants after the beginning of the application of the stimulating signal (S(t)).

2. Device as claimed in claim 1, wherein said controlling element comprises a timing element configured for applying said stimulating signal for a predetermined period of time Td and analysing the initial portion of the waveform of curve $C_{GT}$ to detect a minimum value of the curve $C_{GT}$ within the interval t=0 and t=Td.

3. Device as claimed in claim 1, wherein said controlling element is configured for calculating the slope of the waveform of curve $C_{GT}$ after a minimum in curve $C_{GT}$ has been reached.

4. Device as claimed in claim 1, claims, wherein said controlling element comprises a hazard detecting element configured for determining the instantaneous gradient (dG) of said ratio (GT) after a minimum has been reached in said curve $C_{GT}$; said controlling element further comprises a first comparing element configured for comparing the calculated instantaneous gradient dG with at least a reference value ($dG_{ref}$) and selecting a correcting element for performing an urgent correction to the stimulating signal S(t) in order to avoid lesions, damages or irreversible alterations in said substrate.

5. Device as claimed in claim 4, wherein said correcting element is configured to decrease the voltage of the stimulating signal S(t) in order to prevent deterioration in the cells (C).

6. Device as claimed in claim 1, wherein said controlling element comprises a slope determining element configured to calculate the average variation ΔG of said ratio (GT) in a time interval that is successive to the instant Tm wherein a minimum in the curve ($C_{GT}$) has been reached and that has a pre-determined time width; said controlling element further comprising a second comparing element configured to compare the calculated average variation ΔG of said ratio (GT) with a reference interval of ΔG values.

7. Device as claimed in claim 6, wherein said second comparing element performs the following functions: if the calculated average variation ΔG of said ratio (GT) falls within the reference interval (0<ΔG<$ΔG_{obb}$) a continuing element is selected; if the calculated average variation ΔG of said ratio (GT) falls outside the reference interval and it is smaller than both limits delimiting the interval (ΔG<0<$ΔG_{obb}$) an adjusting element is selected; and if the calculated average variation ΔG of said ratio (GT) falls outside the reference interval and it is greater than both limits delimiting the interval (ΔG>$ΔG_{obb}$>0) a correcting element is selected.

8. Device as claimed in claim 7, wherein said adjusting element is configured to increase the voltage of the stimulating signal in order to increase the value of the electric field E(t) applied to the substrate; said adjusting element subsequently selecting said element for calculating and monitoring the instantaneous value of the said ratio (GT) and said controlling element.

9. Device as claimed in claim 7, wherein said continuing element is configured to increase the voltage of the stimulating signal to an objective voltage $V_{opt}$ in order to increase the value of the electric field E(t) applied to the substrate so that the value of said average variation ΔG tends to an expected value $ΔG_{obb}$.

10. Device as claimed in claim 1, wherein said controlling element is configured to detect a minimum of said initial portion of said curve and determining the time Tm at which the minimum is reached.

11. Device as claimed in claim 10, wherein third comparing is provided to compare the detected Tm with threshold values Ttmin and Ttmax; said third comparing element is configured to perform the following operations: if the detected Tm occurs before Ttmin (Tm<Ttmin) then a correcting is selected; if the detected Tm occurs after Ttmax (Tm>Ttmax), then an adjusting is selected; and if the detected Tm occurs between Ttmin and Ttmax, then a is selected.

12. A method for extracting molecules from living cells comprised in a substrate, comprising the step of using the device of claim 1 to generate a controlled stimulating signal applied to living cells by means of electrodes while extracting molecules from the living cells.

13. A method for introducing molecules into living cells comprising the step of using the device of claim 1 to generate a controlled stimulating signal applied to living cells by means of electrodes while introducing said molecules into the living cells.

14. The method for introducing molecules as claimed in claim 13, wherein said molecules comprise one of the following: a DNA or a RNA molecule containing regulatory sequences and sequence coding for therapeutic genes or genes of interest for biomedical or biotechnological purposes; an oligonucleotide, (ribo- or deoxyribo-nucleotide, single or double strand, including the SiRNA), whether natural (phosphodiesters) or modified (inside the backbone of the oligonucleotide, phosphosulfates, or at the extremities, by addition of groups to protect the oligonucleotides from digestion of nucleases; a protein or peptide, whether natural or genetically or chemically modified, extracted from natural sources or obtained by synthesis, or a molecule simulating the structure of a protein or peptide, whatever its structure; a cytotoxic agent, the antibiotic bleomycin or the cisplatinum; a penicillin; and other pharmacological agents.

* * * * *